(12) United States Patent
Frei et al.

(10) Patent No.: US 9,012,529 B2
(45) Date of Patent: Apr. 21, 2015

(54) HOT-MELT COMPOSITION COMPRISING HYDROCOLLOIDS

(75) Inventors: Pia Frei, Rickenbach (CH); Andreas Dobmann, Oberkirch (CH); Judith Nyffeler, Sempach-Stadt (CH)

(73) Assignee: Nolax AG, Sempach Station (CH)

( * ) Notice: Subject to any disclaimer, the term of this patent is extended or adjusted under 35 U.S.C. 154(b) by 259 days.

(21) Appl. No.: 11/572,167

(22) PCT Filed: Jun. 22, 2005

(86) PCT No.: PCT/EP2005/052921
§ 371 (c)(1),
(2), (4) Date: Jan. 16, 2007

(87) PCT Pub. No.: WO2006/008220
PCT Pub. Date: Jan. 26, 2006

(65) Prior Publication Data
US 2008/0051485 A1 Feb. 28, 2008

(30) Foreign Application Priority Data

Jul. 16, 2004 (EP) .................................... 04016789

(51) Int. Cl.
  *B29C 71/04* (2006.01)
  *A61F 15/00* (2006.01)
  *A61L 15/58* (2006.01)
  *A61L 15/60* (2006.01)

(52) U.S. Cl.
  CPC *A61L 15/58* (2013.01); *A61L 15/60* (2013.01)

(58) Field of Classification Search
  USPC .................................. 522/79, 85, 83; 602/56
  See application file for complete search history.

(56) References Cited

U.S. PATENT DOCUMENTS

| | | | |
|---|---|---|---|
| 4,551,490 A | 11/1985 | Doyle et al. | |
| 4,728,642 A * | 3/1988 | Pawelchak et al. | 514/57 |
| 4,738,257 A | 4/1988 | Meyer et al. | |
| 5,284,688 A * | 2/1994 | Hiatt | 428/41.4 |
| 5,302,629 A * | 4/1994 | Berejka | 523/111 |
| 6,025,071 A | 2/2000 | Cameron et al. | |
| 6,190,689 B1 | 2/2001 | Hoffmann et al. | |
| 6,303,731 B1 * | 10/2001 | Carlson et al. | 528/59 |
| 6,326,524 B1 | 12/2001 | Fattman et al. | |
| 6,710,100 B1 * | 3/2004 | Lipman | 523/111 |
| 2003/0060112 A1 | 3/2003 | Rezai et al. | |
| 2003/0109628 A1* | 6/2003 | Bonfanti et al. | 524/507 |
| 2003/0203011 A1* | 10/2003 | Abuelyaman et al. | 424/445 |
| 2004/0221945 A1* | 11/2004 | Williams et al. | 156/235 |

FOREIGN PATENT DOCUMENTS

| | | |
|---|---|---|
| DE | 2631277 | 2/1977 |
| DE | 3438811 | 5/1985 |
| DE | 10008842 | 6/2001 |
| WO | 02/066087 | 8/2002 |
| WO | 2004/083302 | 9/2004 |
| WO | 2004/098668 | 11/2004 |
| WO | WO 2007133199 A1 * | 11/2007 |

OTHER PUBLICATIONS

XP002249742, BASF: "polymerforschung—der Weg zur Innovation URL—http://www.bastde/de/corporate/innovationen/fakten/polymerforschung/Weg zur Inn DWWW-2003-07-31" BASF-Gruppe Fakten Zur Forschung Polymerforschung, Jul. 31, 2003.
BASF, "Converting Technology, Paper Film & Foil Convertech", Mar. 15, 2002, vol. 30, No. 3, pp. 25-27.

* cited by examiner

*Primary Examiner* — Megan McCulley
(74) *Attorney, Agent, or Firm* — Davis & Bujold, PLLC; Michael J. Bujold

(57) ABSTRACT

A hot-melt formulation useful as a wound dressing comprises a chemically crosslinked polymer matrix obtainable from prepolymers crosslinkable by means of photopolymerization. Hydrocolloids are embedded in the chemically crosslinked polymer, matrix. The formulation is obtainable by combining the prepolymers and hydrocolloids, and heating and processing the mixture through a slot die, wherein the mixture has a viscosity of less than 100 Pa*s and a processing temperature of less than 150° C. The prepolymers are crosslinked by means of photopolymerization by irradiation with UV light.

14 Claims, No Drawings

HOT-MELT COMPOSITION COMPRISING HYDROCOLLOIDS

The invention relates to a hot-melt composition, to a process for providing and/or processing such a hot-melt composition, to a process for reducing the occurrence of discolorations during the provision and/or processing of such a hot-melt composition, to a process for the crosslinking, in particular the complete crosslinking, of prepolymers in such a hot-melt composition, to a wound dressing comprising such a hot-melt composition, and to the use of prepolymers, especially prepolymers crosslinkable by induction by irradiation, in accordance with the preambles of the independent claims.

Hydrocolloid pressure-sensitive adhesives are at the present time gaining increasingly in importance in wound-care. In this field the hydrocolloid pressure-sensitive adhesives employed serve both for mechanical stabilization of the wound and as absorbers for the wound secretions that emerge in the course of the healing process. In such adhesives the necessary hydrocolloids are embedded in a continuous phase ("matrix") of thermoplastic rubber. The formulations are typically and preferably formulated in such a way that up to 5 times the amount by weight of water or wound secretion can be absorbed without the integrity of the matrix being lost. Moreover, the medical sector sets conditions which must be met in respect of the necessary skin adhesion.

The thermoplastic rubbers which are presently employed in the art are typically SIS (styrene-isoprene-styrene) or SBS (styrene-butadiene-styrene) block copolymers. Set into these copolymers are polymeric compounds with a high water absorption capacity, typically in powder form. In the course of the healing process, these compounds absorb the secretion emerging from the wound and, in so doing, become swollen. This entails exacting requirements on the cohesive force of the matrix, which even in the swollen state of the hydrocolloids must not lose its mechanical integrity. In order to meet these requirements, it is obligatory to use thermoplastic rubbers with a high molecular weight, which in combination with the absorbent hydrocolloid leads to high melt viscosities for the composition.

The state of the art is comprehensively described by Roger Lipman in *Medical Device & Diagnostic Industry Magazine* 1999, "Hydrocolloid PSAs: New Formulation Strategies".

The known compositions typically possess a melt viscosity in the range from 130° C. to 150° C. of well above 300 Pa*s, and generally in fact of more than 500 Pa*s (cone/plate measurement method in accordance with DIN EN ISO 3219). In this context it is a disadvantage that the compositions can therefore be processed, by application to a backing material, for example, only by means of calender technology under high pressures and temperatures. Widespread hot-melt processing units, conversely, are incapable of processing such compositions, on account of the high melt viscosity. Typically the processing in hot-melt processing units such as slot dies, rolls, etc., for example, is made considerably more difficult even with melt viscosities of 100 Pa*s; lower melt viscosities are therefore preferred for processing in such units.

Furthermore, frequently, an unwanted but unavoidable discoloration of the compositions is observed if the high melt viscosity of the prior-art compositions is circumvented by means of higher heating. In addition, a multiplicity of hydrocolloids, such as celluloses and pectins, for example, cannot be heated very highly (typically for only a very short period above about 100° C.), which likewise imposes narrow limits on reducing the melt viscosity by increasing the processing temperature.

U.S. Pat. No. 4,738,257 describes a wound dressing featuring a layer of polyisobutylene and ethylene-vinyl acetate resin. Hydrocolloids are set into this mixture. In the course of sterilization, ionizing radiation (electron beam, EP) brings about crosslinking of the ethyl-vinyl acetate resin. A disadvantage with this process too is the need, owing to the excessive melt viscosity at low temperatures, in particular about 130° C. to 150° C., to have to undertake processing by means for example of calenders; with conventional hot-melt application equipment the compositions cannot be processed, in particular at temperatures of about 130° C. to 150° C. Moreover, owing to the layer thickness which is generally necessary, typically of 0.5 mm to 1 mm, it must be assumed that the crosslinking of the ethyl-vinyl acetate resin by means of ionizing radiation will be incomplete, resulting in deficient reproducibility and deficient consistency of quality.

It is an object of the invention, therefore, to avoid the disadvantages of the known, and thus in particular to provide a hot-melt composition with hydrocolloids, preferably for use as a wound dressing, which at relatively low temperatures possesses a melt viscosity such that the ability to carry out processing with conventional hot-melt application equipment is made possible. A further object of the invention is to allow such a composition to be used in the medical sector, and also to achieve results comparable as far as possible with those of known hydrocolloid pressure-sensitive adhesives in respect of the adhesion, the capacity to absorb wound fluid, and the lasting integrity of the matrix.

This object is achieved by a hot-melt composition, by a process for providing and/or processing such a hot-melt composition, by a process for reducing the occurrence of discolorations during the provision and/or processing of such a hot-melt composition, by a process for the crosslinking, in particular the complete crosslinking, of prepolymers in such a hot-melt composition, by a wound dressing comprising such a hot-melt composition, and by the use of prepolymers, especially prepolymers crosslinkable by induction by irradiation, in accordance with the characterizing parts of the independent claims. Further aspects of the object will become apparent to the skilled worker in the context of the description and of the working examples.

A hot-melt composition of the invention comprises
  (a) a chemically crosslinked polymer matrix; and
  (b) hydrocolloids embedded in the chemically crosslinked polymer matrix;
which is obtainable by processing a melt in a hot-melt process, the melt having a melt viscosity of less than 100 Pa*s, preferably of less than 75 Pa*s, more preferably of less than 50 Pa*s, at a processing temperature of less than 150° C., preferably of less than 140° C., more preferably of less than 130° C.

By a hot-melt composition is meant, here and below, compositions which are solid at room temperature and are water-free and solvent-free, particularly adhesives, preferably pressure-sensitive adhesives (hot-melt pressure-sensitive adhesives, HMPSAs), which are processed from the melt, in particular by application to a backing material, and which set physically on cooling, with solidification.

The melt viscosities are determined, here and below, in accordance with DIN EN ISO 3219, cone/plate measurement method.

Through the provision of a melt having a melt viscosity of less than 100 Pa*s, preferably of less than 75 Pa*s, more preferably of less than 50 Pa*s at a processing temperature of less than 150° C., preferably of less than 140° C., more preferably of less than 130° C., it is made possible in the context of the invention to use conventional hot-melt application apparatus such as that, for example, equipped with slot dies or rolls in order to process the melt. Moreover, through the provision of a melt thus characterized, the need for high temperatures, in particular temperatures of more than 150° C., during processing is done away with.

According to one embodiment of the invention the chemically crosslinked polymer matrix is formed from prepolymers crosslinked in particular by induction by irradiation. Suitable prepolymers are selected here in terms of their molecular weight preferably such that they give the resulting hot-melt composition, in particular after crosslinking, strength at room temperature, but in the course of processing, in particular during application to a backing material, they give the melt a viscosity which is suitable for conventional hot-melt application apparatus. Typical melt viscosities in this context are melt viscosities of less than 100 Pa*s, preferably of less than 75 Pa*s, more preferably of less than 50 Pa*s at a processing temperature of less than 150° C., preferably of less than 140° C., more preferably of less than 130° C.

Suitable prepolymers which are crosslinkable by induction by irradiation have (latent or free) reactive functionalities which can be crosslinked by means of an external influence. In the context of the invention preference is given here to crosslinking by means of photopolymerization. Crosslinking by means of EB, however, is of course also possible.

According to one exemplary embodiment, particularly preferred in the context of the invention, UV-crosslinking acrylates are used as prepolymers in the hot-melt composition. By irradiation with high-energy light, especially UV light in the wavelength range from approximately 200 nm to 450 nm, the prepolymers can be induced to crosslink. Particularly preferred UV-crosslinking acrylate prepolymers are those of the acResin® product family from BASF, such as acResin 203 UV or 204 UV, for example. Combinations of such polymers are of course also possible. These substances are notable for copolymerized monomers to which UV-activable photoinitiator groups have been attached chemically using a spacer group. The addition of low molecular mass photoinitiators—which are to be avoided in any case particularly for medical uses—is therefore not necessary to achieve sufficient and rapid crosslinking.

In the context of the invention it is of course likewise possible to provide typical photoinitiators in the hot-melt composition that bring about accelerated onset of the crosslinking of the prepolymer. Suitable photoinitiators of this kind are, for example, acetophenone, benzoin ethers, benzyl dialkyl ketols, for example, or derivatives thereof. The amount of photoinitiator is typically low, preferably 0.05 to 10 parts by weight, more preferably just 0.1 to 2 parts by weight of the hot-melt composition. For medical applications in particular it is especially preferred not to provide any free photoinitiators of low molecular mass; it is therefore possible to provide, with particular preference, copolymerized photoinitiators, examples being ethylenically unsaturated compounds having a photoinitiator group, in a fraction for example of 0.05 to 10 parts by weight, preferably of 0.1 to 2 parts by weight, more preferably of 0.1 to 1 part by weight of the hot-melt composition. Compounds of this kind are known for example from EP-A-346 734, EP-A-377 199 (claim 1), DE-A-40 37 079 (claim 1) or DE-A-38 44 444 (claim 1); the disclosure content of the cited documents in respect of these photoinitiators is hereby declared part of this document.

In a further embodiment of the invention the hot-melt composition comprises prepolymers in a fraction of about 30% to about 80% by weight, preferably of about 40% to about 50% by weight. Such fractions of prepolymers have proven advantageous in order to form a polymer matrix which is mechanically stable even in the swollen state. For this purpose the prepolymers are crosslinked after hot-melt processing.

The hot-melt composition of the invention contains hydrocolloids which are embedded in the polymer matrix and are selected from the group consisting of superabsorbents, especially acrylate-based superabsorbents, carboxylated celluloses, pectins, alginates, vinyl polymers, acrylate polymers and ethylene oxide polymers. Particular preference is given in the context of the invention to superabsorbents, especially acrylate-based superabsorbents. These are more stable thermally than, say, celluloses or pectins, which withstand only for a very short time period a thermal load of up to 130° C., in particular up to 150° C., without suffering discoloration and/or decomposition. Superabsorbents, in contrast, are thermally robust right into this range, without exhibiting discoloration and/or decomposition. Hydrocolloids with an average particle sizes as low as possible, provided in powder form, are preferred in the context of the invention. Used with preference at present in the context of the invention is Superabsorber T 5066 F superabsorbent from Degussa (Stockhausen), having a particle size of 0-63 µm, containing less than 2% by weight of particles with a size of more than 63 µm. In the context of the invention it is of course also possible to use the thermally less stable hydrocolloids such as pectins and celluloses if the further components of the composition, especially the prepolymers, are selected such that it is possible to obtain a melt viscosity for the composition that is suitable for common hot-melt processing units, even below the temperature which is critical for the particular hydrocolloid in question.

It is particularly preferred for the hot-melt composition to embrace the hydrocolloids in a fraction of about 10% to about 40% by weight, preferably of about 15% to about 25% by weight. The capacity for water absorption increases with the fraction of hydrocolloid; high fractions of hydrocolloids are therefore advantageous, but in the swollen state place a heavy load on the polymer matrix. With a composition of the invention containing a polymer matrix comprising prepolymers which have been crosslinked subsequently, it is now possible to realize similarly high fractions of hydrocolloids in compositions of this kind, using conventional hot-melt processing units, as it has been possible to process to date only, for example, by the calender technique.

In further preferred embodiments the hot-melt composition further comprises:

(a) a tackifier, in particular a hydrocarbon-based tackifier, preferably embracing a fraction of about 2% to about 20% by weight, more preferably of about 5% to about 10% by weight; and/or (b) a plasticizer, in particular an adipic acid-based plasticizer, preferably embracing a fraction of about 5% to about 20% by weight, more preferably of about 10% to about 15% by weight; and/or (c) one or more stabilizers, preferably embracing a fraction of up to about 1% by weight, more preferably of up to about 0.5% by weight.

The subsequent crosslinking of the prepolymers raises the average molecular weight of the polymer matrix, thereby producing an increase in the cohesive forces (improving the mechanical integrity of the matrix even in the swollen state); in parallel, however, this leads to a reduction in the tack. Surprisingly, though, in spite of the already high proportions of hydrocolloid and prepolymer (or polymer matrix), it is possible to increase the tack further through addition of suitable tackifiers, especially hydrocarbon-based tackifiers. In particular, copolymers of vinyl methyl ether and maleic acid and/or copolymers of vinyl methyl ether and pyrrolidone are of particular preference for this purpose, provided in particular in anhydride form. Particular preference is given presently in particular to the copolymers of the Gantrez® product family, particularly the Gantrez S product family, from ISP, International Speciality Products, Wayne, N.J. 07470 USA.

Preferred plasticizers present are, in particular, adipic acid-based plasticizers such as Plastomoll DNA from BASF, for example. The selection of a suitable plasticizer by the skilled worker, however, is not subject traditionally to any restrictions, provided they are compatible with the requirements of the intended use, particularly in the medical sector, and allow processing in conventional hot-melt application apparatus.

If it is desired or necessary on account of the intended application, it is also possible to add stabilizers to the composition (for example, from the Irganox product family, e.g., Irganox B612 from Ciba Spezialitatenchemie AG) in fractions which are low in particular. The selection of a suitable stabilizer by the skilled worker, however, is not subject additionally to any restrictions, provided it is compatible with the requirements of the intended use, particularly in the medical sector, and allows processing in conventional hot-melt application apparatus.

The hot-melt composition preferably further comprises an additive which improves the dynamic water absorption capacity, in particular:
  preferably: a sulfonated copolyester, preferably in a fraction of about 5% to about 30% by weight, more preferably in a fraction of about 10% to about 15% by weight; and/or
  a fluorocarbon compound, preferably in a fraction of about 0.5% to about 2% by weight, more preferably in a fraction of about 0.5% to about 1% by weight.

Sulfonated copolyesters in particular, from the AQ product family from Eastman Chemicals, for example, e.g. AQ 1045, improve the dynamic water absorption capacity considerably, which is of advantage especially in a multiplicity of medical applications.

The invention further provides a process for providing and/or processing a hot-melt composition in particular of claim 1, preferably a hydrocolloid pressure-sensitive adhesive formulation, which comprises the following steps:
  (a) adding to the composition at least one crosslinkable prepolymer whose nature and amount are such as to give a melt viscosity of less than 100 Pa*s, preferably of less than 75 Pa*s, more preferably of less than 50 Pa*s, at a processing temperature of less than 150° C., preferably of less than 140° C., more preferably of less than 130° C.;
  (b) processing the composition in a hot-melt process;
  (c) crosslinking the prepolymer of the composition, in particular by irradiation.

In the context of this process it is particularly preferred for the processing in a hot-melt process to encompass application to a release material and to a backing film in what is called a transfer process. In this case, in a hot-melt process, application takes place first to a release material, in particular a siliconized, biaxially oriented polypropylene film (BOPP film), followed subsequently by lamination with a backing film. At the present time, polyurethane-based backing films are used. With particular advantage the release material and, where appropriate, the backing film as well are each selected so as to be substantially transparent to radiation acting subsequently on the composition, particularly on the prepolymers of the composition, such as UV radiation, for example. This allows the irradiation of the composition through the backing film and/or through the release material as well. Irradiation (one side or both sides) takes place preferably, in the context of the invention, in-line with the hot-melt process, in other words essentially directly after the application of the melt to the release material and before lamination with a backing film in a conventional hot-melt processing unit.

After processing in a hot-melt process, in particular including application to a release material, the composition subsequently, preferably likewise in-line with the hot-melt process, is lined and laminated with a backing film, in particular a polyurethane-based backing film. The release material facilitates the provision of the hot-melt composition, for medical purposes for example: The release material can be peeled off with a low level of manual effort, and the hot-melt composition is exposed and can be applied, as a wound dressing for example.

The processing of the composition in a hot-melt process takes place preferably at a melt temperature of not more than 150° C., preferably of not more than 140° C., more preferably of not more than 130° C. It is of course likewise possible in the context of the invention to carry out hot-melt processing at lower temperatures, if at lower temperatures a sufficiently low melt viscosity of not more than 100 Pa*s is already obtained by virtue of the specific formulation, in particular the selected prepolymers.

With particular preference the crosslinking of the prepolymers in the composition is performed or induced after hot-melt processing, in particular in-line, by irradiation, in particular with high-energy UV light (in the wavelength range from about 200 nm to about 450 nm, for example), through the backing film and/or through the liner film. By this means it is possible where appropriate, in the case of relatively large layer thicknesses, to irradiate a sheetlike substrate on both sides as well, thereby making it possible to achieve a decisive improvement in the reliability of complete crosslinking and hence in the consistency of quality.

The invention further provides an absorbent medical or cosmetics article, in particular a wound dressing, such as plasters, compresses, etc., for example, comprising an above-described hot-melt composition, preferably produced using one of the processes described above.

The invention provides, furthermore, for the use of prepolymers, especially prepolymers crosslinkable by induction by irradiation,
  for providing an above-described hot-melt composition; and/or
  in one of the processes described above.

The invention additionally provides a process for reducing the occurrence of discolorations in the provision and/or processing of a hot-melt composition, preferably a hydrocolloid pressure-sensitive adhesive formulation, wherein the provision and/or processing of the hot-melt composition takes place at a melt temperature of not more than 150° C., preferably of not more than 140° C., more preferably of not more than 130° C. As a result of processing up to this temperature range, there are generally no observable instances of discoloration of the composition as a result of thermal stress, which can otherwise be observed in particular with hydrocolloid hot-melt compositions. The generation of the polymer matrix by subsequent crosslinking of the prepolymers, in particular, is what makes these comparatively low processing temperatures possible, thus allowing the provision of pure white or transparent compositions, which as well as enhanced aesthetics also ensure a greater ease of monitoring the healing process of, for example, a covered wound.

The invention is elucidated below with reference to a preferred exemplary embodiment.

A formula which is presently preferred in the context of the invention comprises the following components:

| | |
|---|---|
| 43.2% by weight | acResin A204 UV, BASF (UV-crosslinkable acrylate prepolymer) |
| 13.5% by weight | AQ 1045, Eastman (sulfonated copolyester) |
| 13.5% by weight | Plastomoll DNA, BASF (plasticizer) |
| 7.5% by weight | Gantrez S 97 BF, ISP (tackifier) |
| 22% by weight | Superabsorber T 5066 F, Degussa (Stockhausen) (superabsorbent) |
| 0.3% by weight | Irganox B612, Ciba (stabilizer) |

The components are intimately mixed. The composition is extremely viscous at room temperature. The composition was applied selectively at temperatures of 130° C., 140° C. and 150° C. to a siliconized, biaxially oriented polypropylene film (BOPP film, release material) (200 g/m²) and laminated to a polyurethane-based backing film (100 μm thick) by means of a conventional hot-melt processing unit from Nordson with a slot die. In all cases the melt viscosity was well below the upper limit of about 100 Pa*s that is critical for processing units of this kind; even at 130° C. the melt viscosity was only 25 Pa*s.

The crosslinking of the prepolymers was initiated in-line, directly after hot-melt processing, by exposing both sides using UV Minicure (company IST) exposure devices. The crosslinking dose is 240 mJ/cm² in the UV-C range (250-260 nm). The result is an off-white coating.

The static water absorption of an isotonic, aqueous 0.9% strength NaCl solution was determined after 24 hours' storage of the composition on the backing film at 37° C. and found to be 250% by weight, based on a specimen area of 19.6 cm². The calculation for this takes place as follows:

Absorption in g/m²/24 h:

(((Weight of specimen after 24 h at 37° C.)−(weight of specimen before beginning of test))/19.6 cm²) *10,000=absorption in g/m²/24 h Absorption in %:

(100/(Weight of specimen before beginning of test))* (water absorption in g/24 h)=water absorption in %

The appearance of the test specimen and also of the isotonic solution was subsequently assessed visually:
Integrity of test specimen: OK
Isotonic test solution: transparent
Hot-melt composition: white, compact The skin adhesion was examined in a panel test:
Instantaneous adhesion: good
Adhesion after 1 day: very good
Adhesion after 3 days: very good
Color/appearance after 3 days: slightly turbid-transparent
Removability after 3 days: painless

The invention claimed is:

1. A formulation comprising
   (a) a chemically crosslinked polymer matrix, obtainable from acrylic prepolymers crosslinkable by means of photopolymerization; and
   (b) hydrocolloids embedded in the chemically crosslinked polymer matrix; and
   (c) an additive which improves dynamic water absorption capacity, said additive being a sulfonated copolyester;
   obtainable by
      combining the acrylic prepolymers, hydrocolloids, and the additive which improves dynamic water absorption capacity, and heating and processing the mixture through a slot die at a processing temperature of less than 150° C., wherein the mixture has a viscosity of less than 100 Pa*s, at said processing temperature; and
      crosslinking the acrylic prepolymers by means of photopolymerization by irradiation with UV light.

2. The formulation of claim 1, wherein the formulation is a hydrocolloid pressure-sensitive adhesive.

3. The formulation of claim 1, comprising about 30% to about 80% by weight crosslinked polymer.

4. The formulation of claim 1, wherein the hydrocolloids are selected from the group consisting of superabsorbents.

5. The formulation of claim 4, comprising about 10% to about 40% by weight hydrocolloids.

6. The formulation of claim 1, further comprising a compound chosen from the group consisting of a tackifier, a plasticizer, one or more stabilizers, and mixtures thereof.

7. The formulation of claim 6, wherein the tackifier comprises compounds chosen from the group consisting of copolymers of vinyl methyl ether and maleic acid; copolymers of vinyl methyl ether and pyrrolidone; and mixtures thereof.

8. An absorbent medical or cosmetics article comprising a formulation of claim 1.

9. A process for reducing the occurrence of discolorations in the provision or processing of a formulation of claim 1, wherein the provision or processing of a hot-melt formulation takes place at a melt temperature of not more than 150° C.

10. A process for providing or processing a hydrocolloid pressure-sensitive adhesive formulation, which comprises the following steps:
    a) providing at least one crosslinkable acrylic prepolymer whose nature and amount are such as to give a melt viscosity of less than 100 Pa*s, at a processing temperature of less than 150° C.;
    b) providing hydrocolloids;
    c) providing an additive which improves dynamic water absorption capacity, said additive being a sulfonated copolyester;
    d) combining the acrylic prepolymers, hydrocolloids and the additive which improves dynamic water absorption capacity, and heating and processing the mixture through a slot die, wherein the mixture has a viscosity of less than 100 Pa*s, at a processing temperature of less than 150° C.; and
    e) crosslinking the acrylic prepolymer of the formulation by means of photopolymerization, by irradiation with UV light.

11. The process of claim 10, wherein the mixture is laminated with a backing film before crosslinking.

12. The process of claim 10, wherein the mixture is applied to a release material before crosslinking.

13. The process of claim 12, comprising the step of irradiation through a backing film or the release material, or a double-sided irradiation of a hot-melt situated on the release material.

14. A process for crosslinking acrylic prepolymers in a hot-melt formulation comprising acrylic prepolymers crosslinkable by means of photopolymerization, hydrocolloids and an additive which improves dynamic water absorption capacity, said additive being a sulfonated copolyester, wherein all components are premixed and then applied to a release material, wherein the crosslinking takes place by means of irradiation with UV light.

* * * * *